US011341594B2

(12) United States Patent
Salon et al.

(10) Patent No.: US 11,341,594 B2
(45) Date of Patent: May 24, 2022

(54) PHENOTYPING APPARATUS

(71) Applicants: INSTITUT NATIONAL DE LA RECHERCHE AGRONOMIQUE (INRA), Paris (FR); INOVIAFLOW, Dole (FR)

(72) Inventors: Christophe Salon, Montagny les Seurre (FR); Christian Jeudy, Maxilly sur Saone (FR); Christophe Baussart, Pesmes (FR); Frédéric Chazallet, Marseilles (FR); Mickael Lamboeuf, Dijon (FR); Julien Martinet, Auxonne (FR)

(73) Assignees: INSTITUT NATIONAL DE LA RECHERCHE AGRONOMIQUE (INRA), Paris (FR); INOVIAFLOW, Dole (FR)

(*) Notice: Subject to any disclaimer, the term of this patent is extended or adjusted under 35 U.S.C. 154(b) by 383 days.

(21) Appl. No.: 16/617,298

(22) PCT Filed: May 29, 2018

(86) PCT No.: PCT/EP2018/064057
§ 371 (c)(1),
(2) Date: Nov. 26, 2019

(87) PCT Pub. No.: WO2018/219942
PCT Pub. Date: Dec. 6, 2018

(65) Prior Publication Data
US 2020/0167884 A1     May 28, 2020

(30) Foreign Application Priority Data
May 29, 2017  (EP) ..................... 17173289

(51) Int. Cl.
*G06K 9/00* (2022.01)
*G06T 1/00* (2006.01)
(Continued)

(52) U.S. Cl.
CPC .............. *G06T 1/0007* (2013.01); *A01G 7/00* (2013.01); *G06T 7/0002* (2013.01); *H04N 7/002* (2013.01);
(Continued)

(58) Field of Classification Search
CPC ................. G06T 1/0007; G06T 7/0002; G06T 2207/30188; A01G 7/00; H04N 7/002; H04N 5/2254; G01N 33/0098
See application file for complete search history.

(56) References Cited

U.S. PATENT DOCUMENTS

| | | | |
|---|---|---|---|
| 9,538,124 B2 * | 1/2017 | Lejeune | ................ A01G 31/00 |
| 2006/0207172 A1 * | 9/2006 | McDonald | ............... A01H 3/02 47/58.1 R |

(Continued)

FOREIGN PATENT DOCUMENTS

| | | | |
|---|---|---|---|
| CN | 101658107 A | 3/2010 | |
| CN | 104897575 A | 9/2015 | |

(Continued)

OTHER PUBLICATIONS

Jeudy, Christian, et al. "RhizoTubes as a new tool for high throughput imaging of plant root development and architecture: test, comparison with pot grown plants and validation." Plant methods 12.1 (2016): 1-18. (Year: 2016).*

(Continued)

*Primary Examiner* — Avinash Yentrapati
(74) *Attorney, Agent, or Firm* — Cooper Legal Group, LLC; Ronald M. Kachmarik

(57) ABSTRACT

Apparatus to acquire an image of roots of a plant located in a target rhizotron. The apparatus includes: a turntable having
(Continued)

a rotation axis and intended to support the target rhizotron; a lightening device; a first camera having an optical axis substantially oriented toward the rotation axis; a focus sensor arranged so as to provide a measure at least one parameter of the first camera; a control module, configured to receive the measure, compare the measure to comparison data, and inform an operator accordingly, the comparison data comprising data related to reference rhizotrons different than the target rhizotron, and/or data related to one or several previously acquired images of the target rhizotron.

15 Claims, 2 Drawing Sheets

(51) Int. Cl.
    *A01G 7/00*     (2006.01)
    *G06T 7/00*     (2017.01)
    *H04N 7/00*     (2011.01)
    *G01N 33/00*     (2006.01)
    *H04N 5/225*     (2006.01)

(52) U.S. Cl.
    CPC .............. *G01N 33/0098* (2013.01); *G06T 2207/30188* (2013.01); *H04N 5/2254* (2013.01)

(56) References Cited

U.S. PATENT DOCUMENTS

| | | | |
|---|---|---|---|
| 2011/0116688 A1 | 5/2011 | Li et al. | |
| 2013/0070081 A1 | 3/2013 | Lejeune et al. | |
| 2017/0031053 A1* | 2/2017 | Kumar | G01V 5/0016 |
| 2018/0348186 A1* | 12/2018 | Benfey | G01N 33/0098 |

FOREIGN PATENT DOCUMENTS

| | | |
|---|---|---|
| DE | 102008039456 A1 | 3/2009 |
| EP | 0619905 B1 | 7/1995 |
| EP | 2679088 A1 | 1/2014 |

OTHER PUBLICATIONS

International Search Report from corresponding International Application PCT/EP2018/064057 dated Sep. 5, 2018, 6 pages.
Christian Jeudy, et al.: "RhizoTubes as a new tool for high throughput imaging of plant root development and architecture: test, comparison with pot grown plants and validation", Plant Methods, vol. 12, No. 1, Jun. 7, 2016, DOI:10.1186/s13007-016-0131-9.
Anonymous: "Application Note—Line Scan Imaging Basics", Teledyne Dalsa application notes, Jan. 21, 2003, http://info.teledynedalsa.com/acton/attachment/14932/f-03ce/1/-/-/-/-/00541-00_03-32_Linescan_Imaging_Basics.pdf.
Anonymous, "Understanding Line Scan Camera Applications", Teledyne Dalsa White Papers, Mar. 20, 2014, http://docplayer.net/19654285-Understanding-line-scan-camera-applications.html.
Peter Gips and Ulrich Oechsner: "Line scan cameras for industrial image processing—Practical uses in industry and research", Schäfter+Kirchhoff GmbH, May 8, 2013, https://www.sukhamburg.com/download/Art-Optik+Photonik_2012_7_49_E.pdf.
Anonymous: "Introduction to Line Scan Cameras", Schäfter+Kirchhoff GmbH, Jan. 22, 2017, https://web.archive.org/web/20170122082124/https://www.sukhamburg.com/products/line-scan-cameras/introduction.html.
Samantha Frost: "A Practical Guide to Using the In-Sight 5604 Line Scan Vision System", Cognex, Oct. 10, 2014, http://www.cognex.com/support/downloads/ns/1/11/91/Integration%20Note%20-%20A%20Practical%20Guide%20to%20Using%20In-Sight%20Line%20Scan_Updated%202014-Oct-10.pdf.

* cited by examiner

PHENOTYPING APPARATUS

TECHNICAL FIELD

The present invention relates to the field of observation of the development of plant roots, including selecting plants with traits of interest, including agronomic characters of interest. The present invention relates more particularly to the field of culture and phenotyping plants, for example in plant variety selection processes.

STATE OF THE ART

In order to maintain high yields while saving water and preserving non-renewable resources and thus limiting the use of chemical fertilizer, it is crucial to select plants with more efficient root systems. This could be achieved through an optimization of both root architecture and root uptake ability and/or through the improvement of positive plant interactions with microorganisms in the rhizosphere. The development of devices suitable for high throughput phenotyping of root structures remains a major bottleneck.

INRA has developed specific rhizotrons suitable for plant growth in controlled conditions and non-invasive image acquisition of plant shoot and root systems. These rhizotrons, called "RhizoTubes", are described in EP 2 679 088.

These rhizotrons allow growing one to six plants simultaneously, having a maximum height of 1.1 m, up to 8 weeks, depending on plant species. Both shoot and root compartment can be imaged automatically and non-destructively throughout the experiment thanks to an imaging cabin, called RhizoCab.

RhizoCab contains robots and imaging equipment for obtaining high-resolution pictures of plant roots. It is described in the article "RhizoTubes as a new tool for high throughput imaging of plant root development and architecture: test, comparison with pot grown plants and validation», by Christian Jeudy et al, Plant Methods (2016) 12:31 DOI 10.1186/s13007-016-0131-9.

RhizoCab allows phenotyping of plant shoots and roots under various abiotic and biotic environmental conditions. In particular, it allows an easy visualization or extraction of roots and measurement of root traits for high-throughput or kinetic analyses. It is therefore usable for the identification of genetic and environmental determinants of key root traits involved in crop responses to stresses, including interactions with soil microorganisms.

There is a permanent need to improve the RhizoCab, in particular to obtain high resolution images in a simple and efficient manner.

An object of the present invention is to answer, at least partly, to this need.

SUMMARY OF THE INVENTION

The invention provides an apparatus to acquire an image of roots of a plant located in a target rhizotron, said apparatus comprising:
  an turntable having a rotation axis and intended to support said target rhizotron;
  a lightening device;
  a first camera, or "root camera", having an optical axis, preferably an horizontal optical axis, substantially oriented toward said rotation axis, said first camera comprising a plurality of elemental light sensors, each elemental light sensor being configured to acquire a respective elemental signal.

According to a first aspect of the invention, the apparatus comprises a control module configured to
  i) determine an elemental time period as a function of
    a rotation speed of the turntable around said rotation axis, and
    a distance between said elemental light sensors and said target rhizotron and/or the zoom magnification of the first camera;
  ii) control the elemental light sensors to generate pixel signals from said elemental signals, each pixel signal starting at an initial pixel tick, lasting for said elemental time period, and finishing at a final pixel tick;
  iii) parameterize a pixel of an image according to a respective pixel signal.

As it will be described with more details in the following description, these operations allow for the acquisition of images with so-called "square pixels", even if the distance between the elemental light sensors and the target rhizotron and/or the zoom magnification of the camera change. Advantageously, these operations are simple and do not require a change in the rotation speed of the turntable. Indeed, it is sufficient modifying said elemental time period.

According to a second aspect of the invention, which is compatible with said first aspect, said apparatus comprises:
  a focus sensor arranged so as to provide a measure of at least one parameter of the first camera;
  a control module, configured to receive said measure, compare said measure to comparison data, and inform an operator accordingly,
  the comparison data comprising data related to rhizotrons different than said target rhizotron, or "reference rhizotrons" and/or data related to one or several previously acquired images of the target rhizotron.

Advantageously, the control module can therefore evaluate whether the acquisition conditions are those which were expected. The operator can thereafter take appropriate decisions. This makes the quality of the images provided by the apparatus more reliable.

An apparatus according to the invention preferably further comprises one or more of the following optional features:
  the apparatus comprises an indexer configured to provide indexer ticks for a plurality of preferably regularly distributed angular positions of the turntable around its axis, the control module being configured to determine said initial pixel tick and/or final pixel tick from at least one of said indexer ticks;
  the number of said indexed angular positions, i.e. the number of indexer ticks generated for one turn of the turntable, is preferably greater than 1,000, preferably greater than 5,000, preferably greater than 10,000, preferably greater than 12,000;
  at least one initial pixel tick is an indexer tick;
  the elemental time period of a pixel signal is equal to the division of the period between two indexer ticks by a ratio of a multiplication integer by a division integer;
  said division integer and multiplication integer are depending on a distance between said elemental light sensors and said target rhizotron and/or on the zoom magnification of the first camera;
  the elemental light sensors are superposed along a line parallel to a cylindrical lateral surface of the target rhizotron;
  the elemental time period is inversely proportional to the zoom magnification and/or is proportional to said distance between said elemental light sensors and said target rhizotron;

the turntable is configured to make the target rhizotron turn at a constant speed, independently of said zoom magnification and said distance between said elemental light sensors and said target rhizotron, at least as long as the quantity of light received by said elemental light sensors ranges above a determined threshold;

the apparatus comprises a camera support on which the first camera is mounted, said camera support being configured to guide a movement of the camera, and in particular a movement which changes the distance between the camera and the target rhizotron;

the elemental signal provided by an elemental light sensor is preferably a measure of the luminance of the surface of the target rhizotron which is observed by said elemental light sensor;

the focus sensor is configured to measure the angular position of a lens focusing ring mounted in rotation around the optical axis of the first camera;

the focus sensor comprises a potentiometer, which presents an electrical resistance which depends on said angular position;

the lightening device comprises as interface enabling the operator to define the wavelength(s) and/or the intensity of the light emitted by said the lightening device;

the apparatus comprises a conveyor, said conveyor comprising two parallel belts, the turntable comprising a tray and an actuator cooperating with the tray so as to move it vertically between said belts;

the tray is provided with one or more recesses or reliefs conformed to cooperate with corresponding reliefs or recesses, respectively, of the target rhizotron;

a control module is programmed so that the tray turns around the rotation axis X by a multiple of 360° during the acquisition of an image by said camera;

the conveyor is arranged to convey the target rhizotron from a first station to a second station, the first station comprising said first camera and the second station comprising a second camera arranged to acquire images of the aerial part of the plant in the target rhizotron;

the second camera is mounted so that its optical axis is substantially vertical.

The invention also relates to a method to acquire an image of roots of a plant located in a target rhizotron, said method comprising the following steps:

a) convey the target rhizotron to a first station;
b) focus a camera on the target rhizotron;
c) enlighten the target rhizotron with a light and make the target rhizotron turn around a vertical rotation axis X;
d) while the target rhizotron is being enlightened and is turning, acquire elemental signals with the camera;
e) compose said image by a treatment of said elemental signals.

According to an aspect of the invention, step c) comprises an operation in which an operator defines the wavelength(s) and/or the intensity of the light emitted by said the lightening device.

According to an aspect of the invention, at step a), the target rhizotron is conveyed with a conveyor comprising two parallel belts, and, at the first station, rests on a tray before it is moved vertically between said belts to be separated from said belts.

According to an aspect of the invention, after step d), the target rhizotron is conveyed to a second station and, at the second station, images of the aerial part of the plant in the target rhizotron are acquired. This enables a high throughput.

Preferably, an apparatus according to the invention is used to operate a process according to the invention.

The invention also relates to a kit comprising an apparatus according to the invention and a target rhizotron, resting on the turntable.

The rhizotron preferably comprises one or more of the features of the rhizotron according to the EP 2 679 088.

BRIEF DESCRIPTION OF THE FIGURES

Other features and advantages of the invention will become clear upon reading the following detailed description and by examining the attached drawing, in which.

DETAILED DESCRIPTION

Figure 1:
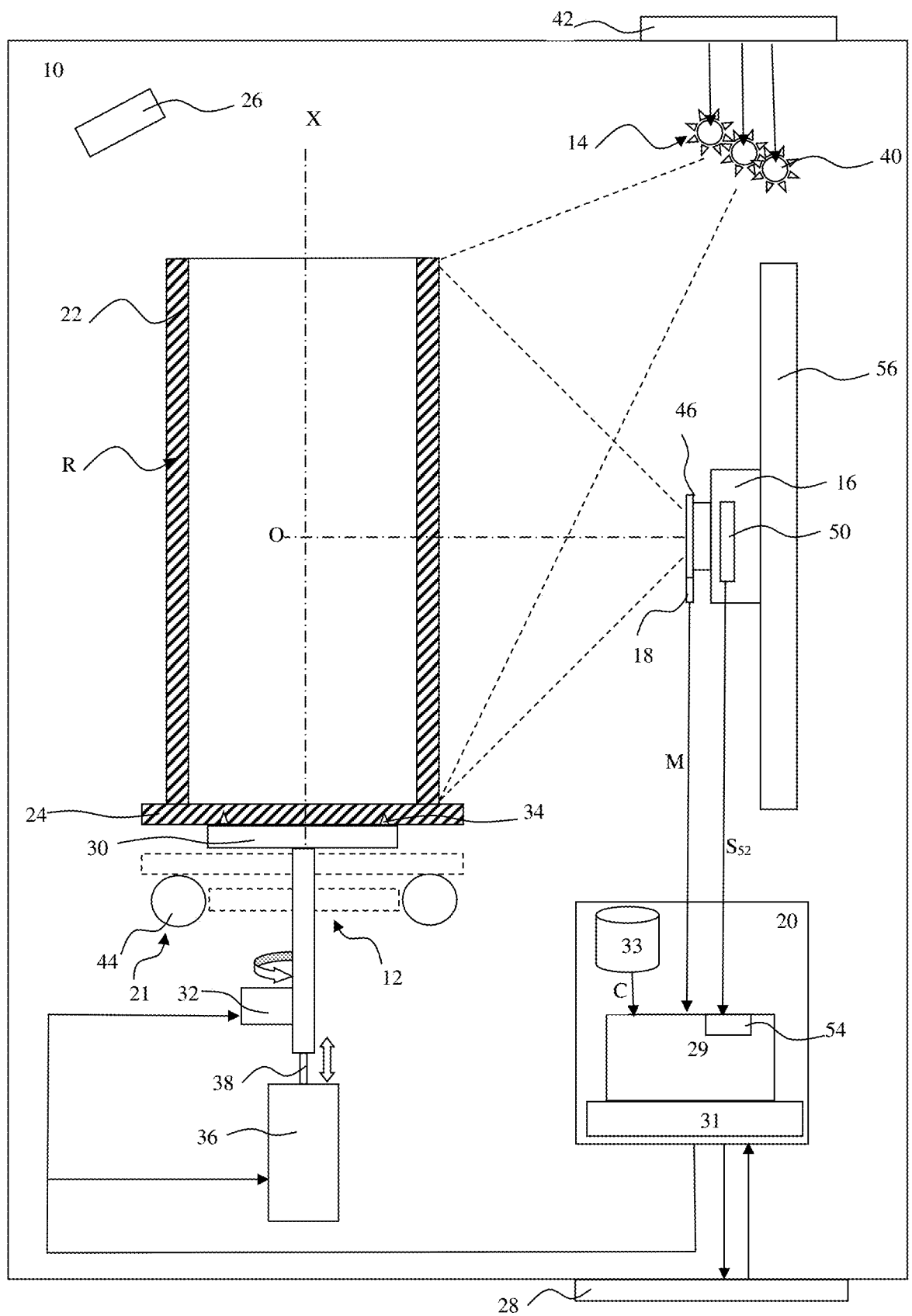
FIG. 1 shows schematically an apparatus according to the invention.

The apparatus represented in FIG. 1 comprises a cab 10 containing a turntable 12, a lightening device 14, a first camera 16, a focus sensor 18 and a control module 20. A target rhizotron R is resting on the turntable.

The apparatus also comprises a conveyor 21 to convey, inside said cab, rhizotrons from the outside of the cab.

Rhizotron

The target rhizotron preferably presents one or several of the features of the rhizotron disclosed in EP 2 679 088.

Typically, it presents the general shape of a vertical tube having a height of about 50 cm, and a diameter of about 20 cm. A plant is planted in the upper opening of the tube. The tube has a cylindrical lateral wall 22 which is transparent, so that the roots of the plant are visible through said lateral wall.

The tube is fixed on a base 24, which closes the lower opening of the tube.

Cab

The cab may be an aluminum and glass cab, preferably about 1.5 m width, 1.5 m deep and 2.5 m high.

Curtains are preferably provided so as to optically isolate the internal volume of the cab from the outside environment, selectively. Preferably, a supervision camera 26 is located inside the cab so as to provide an overview of the turntable 12, and preferably of the first camera 16 and/or of the lightening device 14. The apparatus preferably comprises an interface 28, which is located outside the cabin.

Turntable

The turntable comprises a horizontal tray 30 and a motor group 32 mechanically coupled with said tray to make it turn around a vertical rotation axis X.

The motor group preferably comprises a brushless motor, an indexer 35 and gears coupling said motor with the tray. The motor group may alternatively comprise a stepping motor.

The indexer 35 preferably provides a signal, or "indexer tick", for each of $N_{35}$ regularly distributed angular positions of the turntable around the axis X. For instance, $N_{35}$ may be 3,600 so that an indexer tick is emitted by the indexer after a rotation of 360°/3,600, i.e. 0.1° of the turntable. The time period between two consecutive indexer ticks is called the "indexer time period", $\Delta t_{35}$.

The tray is preferably provided with fixing means, so as to temporarily immobilize the target rhizotron on the tray.

In the preferred embodiment, the turntable comprises clamping means, not represented, arranged so as to tighten the rhizotron on the tray. The clamping means may be constituted by jaws of a pincer or by clamps, for instance.

The tray is preferably provided with one or more recesses or reliefs 34 conformed to cooperate with corresponding reliefs or recesses, respectively, of the target rhizotron. The recesses and/or reliefs of the tray are preferably extending along a vertical axis. Preferably, the tray comprises at least two recesses and/or reliefs so as to limit the rotation of the target rhizotron relative to the tray.

The turntable preferably comprises means to move the tray vertically.

Preferably, the turntable comprises an actuator 36, preferably an hydraulic actuator, said actuator comprising a vertical cylinder rod 38 cooperating with the tray 30 so as to move it vertically.

Lightening Device

The lightening device 14 may provide white light or monochromatic light. The spectrum of wavelengths of the light generated by the lightening device may extend from infrared to ultraviolet.

In the preferred embodiment, the lightening device 14 comprises several lamps 40, preferably comprising three types of LED lamps, preferably emitting a light spectrum centered on 465 nm, 525 nm, and 625 nm wavelengths, respectively. The number of lamps 40 is function of the height of the target rhizotron.

The lamps 40 are synchronized with the image acquisition process of the first camera, according to well-known solutions.

The lamps are preferably oriented so as to homogeneously highlight the target rhizotron R (which is not the case in the schematic FIG. 1).

Preferably, the lightening device comprises as interface 42 enabling the operator to define the wavelength(s) and/or the intensity of the incident light.

First Camera

The first camera 16 is preferably a high definition camera, preferably a Basler raL12288-8gm camera provided with a Zeiss 50 mm f/2 Makro-Planar lens.

The first camera is mounted so that its optical axis O is substantially horizontal and oriented toward the rotation axis X of the turntable. However, preferably, the angle between the optical axis O and the plane containing the rotation axis of the turntable and the light sensor of the first camera is greater than 2°, preferably greater than 4°. Prejudicial reflection is thereby reduced. Preferably, the angle is less than 20°, less than 10°. Preferably, the minimal distance between the two axes O and X is less than 5 cm, preferably less than 2 cm, and greater than 0.5 cm, preferably greater than 1.0 cm.

The first camera comprises a light sensor 50 comprising a plurality of preferably superimposed elemental light sensors 52, preferably more than 5,000 or more than 10,000 elemental light sensors 52, for instance 12,000 superimposed elemental light sensors, preferably extending along a vertical line, parallel to the lateral surface of the target rhizotron.

During the acquisition of an image, each elemental light sensor 52 acquires an elemental signal $S_{52}$.

Figure 2:
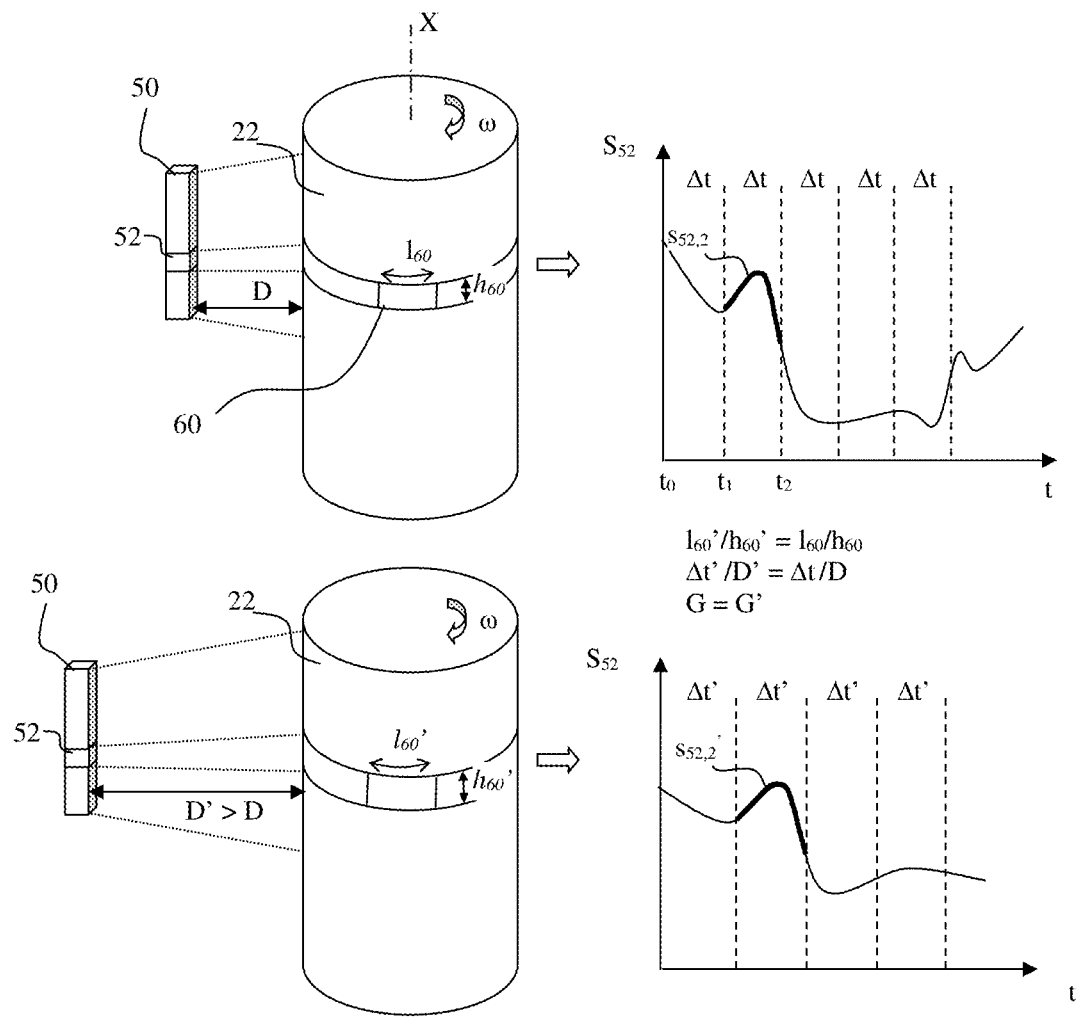
FIG. 2 illustrates the acquisition of an image, in two situations differing by the distance D and D' between the camera and the rhizotron. In the second situation, all the references are affected with a mark "'"

The elemental signals $S_{52}$ is a measure of the luminance of the light that the elemental light sensor receives (FIG. 2).

Figure 3:
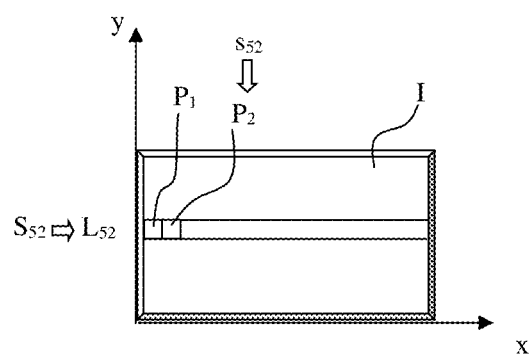
FIG. 3 illustrates said image.

The apparatus comprises an electronic circuit 54 to analyze the elemental signal $S_{52}$ so as to represent it as a line $L_{52}$ of pixels $P_i$ of an image I (FIG. 3).

More precisely, the acquisition of the signal $S_{52}$ by an elemental light sensor 52 starts at instant $t_0$. The target rhizotron is turning and, during an elemental time period $\Delta t$, until instant $t_1$, the elemental sensor 52 receives light reflected and diffused by the target rhizotron and integrates this light during an integration period σ.

For the sake of clarity, the integration period σ is regarded as equal to the elemental time period. In practice, it is slightly less than said elemental time period to include a short processing period.

The result of this integration is a value $V_1$ which is used to parameter the first pixel $P_1$ of the line $L_{52}$ corresponding to the elemental light sensor 52. The portion of the elemental signal $S_{52}$ corresponding to the first pixel is called "pixel signal" $s_{52,1}$.

After instant $t_1$, the elemental sensor 52 receives light and the electronic circuit 54 integrates the light during the integration period of another elemental time period $\Delta t$ (i.e. between instant $t_1$ ($=t_0+\Delta t$) and instant $t_2$ ($=t_1+\Delta t$)). The integration of the light during this second elemental time period is used to calculate the value $V_2$. The electronic circuit 54 then parameterizes the second pixel $P_2$ of the line $L_{52}$ with the value $V_2$. The portion of the elemental signal $S_{52}$ corresponding to the second pixel is the pixel signal $s_{52,2}$.

These operations are repeated for each pixel $P_i$ of the line $L_{52}$.

The number of pixels along the axis x of the image I is therefore equal to the acquisition time period for a line $L_{52}$ divided by $\Delta t$.

All the elemental signals acquired by each elemental light sensor are treated in the same way so as to produce 12,000 superimposed lines of pixels, the superimposition of these lines constituting said image I.

The resolution of the image I along the axis y defining the height of the image I, i.e. the number of lines, or the number of pixels along this axis, therefore depends on the number of elemental light sensors 52. It does not depend on the rotation speed w of the rhizotron. On the contrary, for the same rotation angle of the target rhizotron, the number of pixels along a line, i.e. along the axis x perpendicular to the axis y, increases as the elemental time period $\Delta t$ decreases and decreases as the elemental time period $\Delta t$ increases.

The first camera is preferably mounted on a camera support 56 so that it can be moved, at least in two dimensions, preferably in the three dimensions of the space, according to the operator's needs. In particular, the distance D between the surface of the target rhizotron and the light sensor 50 of the first camera may be modified, to become D'. In a preferred embodiment, the camera support 56 is provided with an actuator to change the position of the camera. Preferably, the actuator of the camera support 56 is controlled by the control module 20.

The first camera may also be provided with a zoom to modify the zoom magnification G.

When the distance D is increased to become D' (FIG. 2) and/or the zoom magnification G is decreased, the first camera observes a larger part of the lateral surface of the target rhizotron, or "observed surface". The general magnification, i.e. integrating the effects of the distance and of the zoom magnification, therefore decreases.

Preferably, to make the interpretation of the image I easier, the number of pixels per cm of the observed surface along the x axis should be the same as along the y axis, independently of the distance D, or of the zoom magnification G. Such pixels are said to be "square".

When the distance D increases or the zoom magnification G decreases, the height of the surface which is observed by the light sensor 50 is increased, i.e. each pixel represents, along the axis y, an increased height of the lateral surface of the target rhizotron.

But if the rotation speed w of the target rhizotron is constant, for a determined acquisition time period, the length, along the circumference of the target rhizotron, which passes in front of the light sensor 50 is not modified, so that, along the axis x, the same length along the circumference of the target rhizotron is represented. The image I therefore represents a view of the lateral surface of the target rhizotron which is laterally compressed, since, for the same dimensions of the image, the height of the observed surface is increased, but not its length. The pixels are not square any more, and the image seems longer along the axis x than along the axis y.

According to the invention, the elemental time period $\Delta t$ depends on the distance D and on the zoom magnification G, and preferably varies in proportion with the distance D and in an inverse proportion with the zoom magnification G.

The ratio between the length $l_{60}$ and the height $h_{60}$ of the elemental surface of the observed surface 60 of the target rhizotron which is used by an elemental light sensor to determine the luminance of a pixel therefore remains the same. Preferably, this ratio remains equal to 1.

As explained previously, each pixel is associated with two instants or "initial and final pixel ticks", at which the integration of the light starts and stops, i.e. $t_0$ and $t_1$ for the first pixel for instance. Pixel ticks are separated by the elemental time period $\Delta t$.

The pixel ticks are preferably generated from the indexer ticks, by the electronic circuit 54. The acquisition of a pixel signal is therefore depending on the angular position of the turntable around its axis. Advantageously, an optimal image is acquired even if the speed of the turntable is modified.

Preferably, the electronic circuit 54 comprises a divider and a conventional phase lock loop (PLL) so as to generate the pixel ticks. The PLL and divider are configured to divide the indexer time period $\Delta t_{35}$ by a ratio p/d, p being a multiplication integer and d being a division integer, so as to generate pixel ticks separated by an elemental time period $\Delta t$, i.e. $\Delta t = \Delta t_{35}/(p/d)$. The value of the ratio p/d is function of a distance between said elemental light sensors and said target rhizotron and/or a function of the zoom magnification of the first camera. The value of the ratio p/d preferably varies in proportion with the distance D and in an inverse proportion with the zoom magnification G.

Advantageously, the combination of a PLL and a divider associated with the indexer enables a simple and optimal synchronization of the mechanical movement of the turntable with the generation of the pixel ticks.

Conveyor

Preferably, the conveyor 21 is arranged to convey the target rhizotron at the location of the turntable 12.

Preferably, the conveyor comprises two parallel belts 44. Preferably the belts have the shape of rolling tubes.

When viewed from above, the tray 30 is located between said belts, ready for the acquisition of images.

The actuator of the turntable is configured so as to move the tray between lower and upper positions in which the tray rests on the belts (position represented in dashed line) and is above the belts, respectively.

In the upper position, the tray may therefore turn around the rotation axis, without being in contact with the belts.

In one embodiment, the apparatus comprises a first station and a second station, which are in connection through the conveyor. In one embodiment, the first station comprises said first camera and the second station comprises a second camera, or "shoot" camera, arranged to acquire images of the aerial part of the plant in the target rhizotron (shoot system). The second camera is preferably mounted so that its optical axis is substantially vertical.

Advantageously, the position of the target rhizotron at the second station is depending on its position at the first station. In particular, preferably, at the first station, the target rhizotron is turned around the rotation axis X by a determined angle, for instance by a number of complete turns (i.e. by a multiple of 360°), so that its position relative to the conveyor is the same after the acquisition of images at the first station as before said acquisition. When the target rhizotron arrives at the second station, its position relative to the conveyor is therefore known.

Advantageously, it is therefore much easier to compare the images acquired at the first station with the images acquired at the second station. In particular, it becomes much easier comparing the geometry of the root system with the geometry of the shoot system.

Focus Sensor

Preferably, the focus sensor evaluates a measure M of a parameter which value depends on the focus of the first camera.

In the preferred embodiment, the focus sensor 18 measures the angular position of a lens focusing ring 46, conventionally mounted in rotation around the optical axis O of the first camera 16. Preferably, the apparatus comprises a potentiometer which is mechanically coupled to the ring. A change of the angular position of the ring therefore modifies the electrical resistance of the potentiometer. In the preferred embodiment, the focus sensor is configured to measure the resistance of the potentiometer so as to evaluate the angular position of the ring.

The potentiometer can be used to set an approximate initial angular position of the ring, for instance when the zoom magnification G and/or a distance D have been changed. The angular position of the ring is thereafter finely tuned starting from this position. Advantageously, the time necessary to correctly position the ring is reduced.

Control Module

The control module 20 may comprise a computer of the prior art, programmed with a software. It conventionally comprises the human-machine interface 28, in particular a screen, a processing unit 29, a communication unit 31 to communicate with the different components, in particular the first camera, the focus sensor, the lightening device and the motor, as well as a memory 33 containing a database.

Preferably, the control module contains the electronic circuit 54 which is used to treat the signals received from the light sensor 50.

The database contains comparison data C related to prior measures of the same parameter, measured on the target rhizotron and/or other rhizotrons, or "reference rhizotrons".

Functioning

Initially, the operator choses a general magnification, i.e. a zoom magnification G and/or a distance D.

The target rhizotron R is preferably carried by the two belts 44 of the conveyor 21, and conveyed into the cab 10, than immobilized above the tray 30 of the turntable 12. The actuator 36 then moves the tray vertically, upwardly, until the tray comes into contact with the rhizotron, and the reliefs 34 of the tray cooperate with the corresponding recesses of the target rhizotron R. The actuator then moves further the tray until the target rhizotron is not in contact with belts any more, as represented in FIG. 1.

The control module 20 then controls the camera support 56 to position the camera at the distance D of the target rhizotron and to set the zoom at the zoom magnification G, according the operator's choice.

At the same time, the first camera 16 then focusses on the target rhizotron R. This focus is conventionally obtained by the rotation of the lens focusing ring 46 of the camera.

The focus sensor 18 measures the angular position of the ring corresponding to the optimal focus, as determined by the camera, and communicates this measure M to the control module 20.

Preferably, the control module compares said measure M with prior measures of the same parameter. The prior measures may relate to the target rhizotron and/or to comparable reference rhizotrons, i.e. having identical or similar characteristics as the rhizotron under analysis.

The control module informs the operator accordingly, through the interface 28. If the comparison does not lead to the detection of an abnormal situation, the control module preferably does not send any information to the interface. Otherwise, it informs the operator.

In particular, preferably, if a focus parameter is substantially different from that which was expected, i.e. in case of an abnormal situation, the control module informs the operator of the discrepancy. The operator may then check the target rhizotron, and in particular its positioning relative to the turntable, and the functioning of the apparatus.

Preferably, the measures M of the parameter are saved. In one embodiment, the control module may therefore detect a drift of the values of the parameter.

If in one embodiment, the control module precludes the acquisition of images of the target rhizotron if an abnormal situation is detected.

If the situation is regarded as normal, the acquisition of the image may start.

Previously, the operator may select and configure one or several lamps of the lightening device so that they emit respective lights having different spectrum, and/or intensities. Advantageously, the operator may therefore choose an incident light which is optimal for his purpose.

The motor makes the tray turn around the vertical rotation axis X at a constant rotation speed $\omega$, whereas the lightening device enlightens the target rhizotron R. At the same time, the camera takes a plurality of 1 pixel wide×12000 pixels high "line images", which are assembled so as to constitute an image of the lateral face of the rhizotron. One turn may be achieved in last than 30 s, preferably less than 20 s, preferably within 10 s.

The indexer 35 generates indexer ticks at predetermined angular positions around the axis X, at instants depending on the rotation speed of the turntable. The indexer ticks are separated by a constant indexer time period $\Delta t_{35}$ since the rotation speed of the turntable is constant.

From the indexer time period $\Delta t_{35}$, the electronic circuit 54 determines an elemental time period $\Delta t$ according to the distance D and the zoom magnification G, preferably to obtain square pixels. Pixel ticks separated by the elemental time period $\Delta t$ are generated consequently.

The integers p and d for the PLL and the divider are determined accordingly.

It generates pixel ticks accordingly.

At a first initial pixel tick $t_0$, corresponding to an indexer tick, the signal received from each elemental light sensor is integrated, by the electronic circuit 54, during the integration time $\sigma$.

There is a short period of time, called "processing period", needed to read the value measured by an elemental light sensor during an elemental time period. The "integration period" during which light is integrated is therefore always slightly less than $\Delta t$. For clarity, the processing period is ignored and it is considered that the integration period is equal to the elemental time period $\Delta t$, i.e. lasts until the final pixel tick $t_1$.

The elemental light sensor may provide analogical signals as represented in FIG. 2. However, preferably, the elemental light sensor is configured to provide digital values or to provide a signal having a staircase shapes.

The initial pixel tick of the next pixel is preferably the final pixel tick $t_1$.

This process is repeated so as to parameterize all the pixels of each line.

In the preferred embodiment, the electronic circuit 54 calculates an elemental time period $\Delta t$ taking into account the distance D and the zoom magnification G so as to obtain square pixels, and analyses all the elemental signals $S_{52}$ received from the elemental light sensors 52 to obtain successive pixel signals $s_{52,i}$ which each lasts said elemental time period $\Delta t$. Each pixel signal $s_{52,i}$ is thereafter converted into a value $V_{52,i}$ which is used to parameterize a corresponding pixel $P_i$.

In an embodiment, several acquired images are combined by the camera to produce a final image. In particular, the three images resulting from the enlightening of the target rhizotron with monochromic lights having red, green and blue colors, respectively, may be superimposed to reproduce a natural color final image. Advantageously, this final image has a very high resolution, each pixel of the light sensor of the camera being used for each of the three images.

The resolution of the final images obtained with the above-described camera ranges from 42 µm per pixel at 600 ppi down to 7 µm per pixel at 3600 ppi. It allows detection of the thinnest roots and nodules and to see hyphae. Image acquisition is very easy and fast.

In addition, square pixels can be easily obtained, without any change in the rotation speed $\omega$, with different distance D and zoom magnification G.

The determination of the elemental time period $\Delta t$ depends on the rotation speed w of the turntable. Preferably, the rotation speed $\omega$ is not modified as the general magnification changes.

Also, preferably, the quantity of light projected by the lightening device 14 is not modified as the general magnification changes.

However, in a preferred embodiment, when the elemental time period $\Delta t$ is below a determined threshold, the rotation speed $\omega$ is reduced and/or said quantity of light is increased when the distance D is reduced and/or when the zoom magnification G is increased. Advantageously, the reduction of the rotation speed $\omega$ and the increase of said quantity of light allows for the integration of at least a minimal quantity of light during said elemental time period $\Delta t$, which improves the quality of the image.

Example

An image I along the whole circumference of the rhizotron is to be acquired. 5,000 indexer ticks are generated for each turn.

The light sensor 50 comprises 12,000 superimposed elemental light sensors, extending along a vertical line, parallel to the lateral surface of the target rhizotron. The number of pixel ticks to be generated directly depends on the number of superimposed elemental light sensors. In the example, it is assumed that, at a first general magnification, a line of the image of the whole circumference of the rhizotron must be constituted by 12,000 pixels to obtain square pixels.

To generate the corresponding 12,000 pixel ticks from the 5,000 indexer ticks, the indexer time period $\Delta t_{35}$ is multiplied by 5 and divided by 12 to obtain the elemental time period $\Delta t'$ between two consecutive pixel ticks. To this end, p and d are set to 12 and 5, respectively.

A change in the rotation speed ω does not modify the number of pixel ticks to be generated, but only the indexer time period $\Delta t_{35}$ and the elemental time period $\Delta t'$.

If the rotation speed ω is 1 turn per 10 s, the indexer time period $\Delta t_{35}$ is therefore 1 ms, and the elemental time period $\Delta t'$ is equal to $^{10}/_{12,000}$=833 μs.

If the rotation speed ω is 1 turn per 5 s, the indexer time period $\Delta t_{35}$ is therefore 0.5 ms, and the elemental time period $\Delta t'$ is equal to $^{5}/_{12,000}$=416 μs.

To shift to a second general magnification, the distance D is for instance divided by 2 and the zoom magnification G is not modified. At the second general magnification, the elemental time period should therefore be $\Delta t=\Delta t'/2=416$ μs to obtain square pixels. 24,000 pixel ticks are therefore generated during one turn of the turntable.

To obtain the 24,000 pixel ticks, $\Delta t_{35}$ ($=^{10}/_{5,000}$ s) is simply multiplied by 5 and divided by 24. To this end, p and d are set to 24 and 5, respectively.

If $\Delta t$ is too low to enable enough light to be integrated by the elemental light sensors between too consecutive pixel ticks, the light provided by the lightening device is increased and/or the rotation speed is reduced.

As it is clear from the preceding description, the invention provides an efficient apparatus which provides reliable images of the roots. In particular, the acquired images may be used as a basis for development of crops that can better manage the effects of limited water or nutrient supply. This will also allow functional validation of the roles of genes.

The invention claimed is:

1. Apparatus to acquire an image of roots of a plant located in a target rhizotron, said apparatus comprising:
    a turntable having a rotation axis and intended to support said target rhizotron;
    a lightening device;
    a first camera having an optical axis substantially oriented toward said rotation axis, said first camera comprising a plurality of elemental light sensors, each elemental light sensor being configured to acquire a respective elemental signal;
    a focus sensor arranged so as to provide a measure at least one parameter of the first camera;
    a control module, configured to receive said measure, compare said measure to comparison data, and inform an operator accordingly,
        the comparison data comprising data related to reference rhizotrons different than said target rhizotron, and/or data related to one or several previously acquired images of the target rhizotron.

2. Apparatus according to claim 1, wherein the focus sensor is configured to measure the angular position of a lens focusing ring, mounted in rotation around the optical axis of the first camera.

3. Apparatus according to claim 2, wherein the focus sensor comprises a potentiometer, which presents an electrical resistance which depends on said angular position.

4. Apparatus according to claim 1, wherein the lightening device comprises as interface enabling the operator to define the wavelength(s) and/or the intensity of the light emitted by said the lightening device.

5. Apparatus according to claim 1, comprising a conveyor, said conveyor comprising two parallel belts, the turntable comprising a tray and an actuator cooperating with the tray so as to move it vertically between said belts.

6. Apparatus according to claim 5, wherein the tray is provided with one or more recesses or reliefs conformed to cooperate with corresponding reliefs or recesses, respectively, of the target rhizotron.

7. Apparatus according to claim 1, wherein the control module is programmed so that the tray turns around the rotation axis by a multiple of 360° during the acquisition of an image by said camera.

8. Apparatus according to claim 5, wherein the conveyor is arranged to convey the target rhizotron from a first station to a second station, the first station comprising said first camera and the second station comprising a second camera arranged to acquire images of the aerial part of the plant in the target rhizotron.

9. Apparatus according to claim 8, wherein the second camera is mounted so that its optical axis is substantially vertical.

10. Apparatus according to claim 1, wherein the control module is configured to evaluate the evolution of said parameter.

11. Apparatus according to claim 1, wherein the control module is configured to
    i) determine an elemental time period as a function of
        a rotation speed of the turntable around said rotation axis, and
        a distance between said elemental light sensors and said target rhizotron and/or the zoom magnification of the first camera;
    ii) control the elemental light sensors to generate pixel signals from said elemental signals, each pixel signal starting at an initial pixel tick, lasting for said elemental time period, and finishing at a final pixel tick;
    iii) parameterize a pixel of an image according to a respective pixel signal.

12. Apparatus according to claim 11, wherein the elemental light sensors are superposed along a line parallel to a cylindrical lateral surface of the target rhizotron.

13. Apparatus according to claim 11, wherein the turntable is configured to make the target rhizotron turn at a constant speed, independently of said zoom magnification and said distance between said elemental light sensors and said target rhizotron.

14. Apparatus according to claim 11, wherein the turntable is configured to make the target rhizotron turn at a constant speed, independently of said zoom magnification and said distance between said elemental light sensors and said target rhizotron, as long as the quantity of light received by said elemental light sensors ranges above a determined threshold.

15. Apparatus according to claim 1, comprising a camera support on which the first camera is mounted, said camera support being configured to guide a movement of the camera which changes the distance between the camera and the target rhizotron.

* * * * *